(12) United States Patent
Várkuti et al.

(10) Patent No.: US 12,133,694 B2
(45) Date of Patent: Nov. 5, 2024

(54) DETERMINING A CONSENSUS PLANE FOR IMAGING A MEDICAL DEVICE

(71) Applicant: Brainlab AG, Munich (DE)

(72) Inventors: Bálint Várkuti, Munich (DE); Rebecca Rittstieg, Munich (DE)

(73) Assignee: Brainlab AG, Munich (DE)

( * ) Notice: Subject to any disclaimer, the term of this patent is extended or adjusted under 35 U.S.C. 154(b) by 1002 days.

(21) Appl. No.: 16/973,181

(22) PCT Filed: Jul. 30, 2018

(86) PCT No.: PCT/EP2018/070621
§ 371 (c)(1),
(2) Date: Dec. 8, 2020

(87) PCT Pub. No.: WO2020/025104
PCT Pub. Date: Feb. 6, 2020

(65) Prior Publication Data
US 2021/0251694 A1 Aug. 19, 2021

(51) Int. Cl.
*A61B 34/20* (2016.01)
*A61B 6/00* (2024.01)
(Continued)

(52) U.S. Cl.
CPC ............ *A61B 34/20* (2016.02); *A61B 6/032* (2013.01); *A61B 6/12* (2013.01); *A61B 6/545* (2013.01);
(Continued)

(58) Field of Classification Search
CPC ......... A61B 34/20; A61B 34/10; A61B 6/032; A61B 6/12; A61B 6/545; A61B 6/4441;
(Continued)

(56) References Cited

U.S. PATENT DOCUMENTS

| 2006/0153468 | A1 | 7/2006 | Solf et al. |
| 2009/0285366 | A1 | 11/2009 | Essenreiter et al. |
| 2016/0166336 | A1* | 6/2016 | Razzaque ............. A61B 34/20 606/130 |

FOREIGN PATENT DOCUMENTS

| EP | 2119397 A1 | 11/2009 |
| WO | 2016097323 A1 | 6/2016 |

OTHER PUBLICATIONS

International Search Report and Written Opinion for corresponding International Application No. PCT/EP2018/070621, dated Apr. 23, 2019. 11 pages.

(Continued)

*Primary Examiner* — Peter Luong
(74) *Attorney, Agent, or Firm* — Tucker Ellis LLP

(57) ABSTRACT

Disclosed is a computer-implemented method of determining a consensus plane for imaging an elongate medical device such as an electrode or a catheter. When positioning an analytical device such that its imaging plane is parallel to or coincides with the consensus plane, an optimal image of the elongate medical device can be generated. The consensus plane is determined by analyzing patient image data used for planning an imaging procedure, planned trajectory data defining a planned position of the elongate medical device relative to the position of an anatomical body part, imaging device constraint data describing machine constraints governing operation of the medical imaging device, avoidance region position data defining the position of anatomical regions of the patient's body, and orientation condition data defining a boundary condition for an angle between the orientation of the consensus plane and the orientation of the characteristic geometric quantity of the elongate medical device.

20 Claims, 6 Drawing Sheets

(51) Int. Cl.
    A61B 6/03    (2006.01)
    A61B 6/12    (2006.01)
    A61B 34/10   (2016.01)
    A61M 5/14    (2006.01)
    A61N 1/05    (2006.01)

(52) U.S. Cl.
    CPC ............ *A61M 5/14* (2013.01); *A61B 6/4441* (2013.01); *A61B 2034/107* (2016.02); *A61B 2034/2065* (2016.02); *A61N 1/0534* (2013.01)

(58) Field of Classification Search
    CPC ....... A61B 6/0487; A61B 6/08; A61B 6/5258; A61B 2034/107; A61B 2034/2065; A61B 2090/376; A61M 5/14; A61N 1/0534; A61N 1/0529; G06T 2207/10116

See application file for complete search history.

(56) References Cited

OTHER PUBLICATIONS

AJNR (http://www.ajnr.org/content/early/2017/08/24/ajnr.A5386) Reply to "Regarding Determining the Orientation of Directional Deep Brain Stimulation Electrodes Using 3D Rotational Fluoroscopy" P.C. Reinacher et al, Aug. 24, 2017. 4 Pages.

Vercise PC with Neural Navigator 2, http://www.bostonscientific.com/en-EU/products/deep-brain-stimulation-systems/Vercise-PC-DBS.html, retrieved 2018. 3 Pages.

Ziv Yaniv, "Fluoroscopic X-ray Image Processing and Registration for Computer-Aided Orthopedic Surgery". Oct. 1, 1998.

Roger Y. Tsai, "A Versatile Camera Calibration Technique for High-Accuracy 3D Machine Vision Metrology Using Off-the-Shelf TV Cameras and Lenses", IEEE Journal of Robotics and Automation, vol. RA-3, No. 4, Aug. 1987, pp. 323-344.

Roger Y. Tsai, "An Efficient and Accurate Camera Calibration Technique for 3D Machine Vision", Proceedings of the IEEE Conference on Computer Vision and Pattern Recognition. Miami Beach, Florida, 1986, pp. 364-374.

* cited by examiner

CT

Rotational fluoroscopy/x-ray

DETERMINING A CONSENSUS PLANE FOR IMAGING A MEDICAL DEVICE

RELATED APPLICATION DATA

This application is a national phase application of International Application No. PCT/EP2018/070621 filed Jul. 30, 2018, the contents of which are incorporated herein by reference.

FIELD OF THE INVENTION

The present invention relates to a computer-implemented method for determining a consensus plane usable for imaging an anatomical body part with a medical imaging device, a corresponding computer program, a non-transitory program storage medium storing such a program and a computer for executing the program, as well as a medical system comprising an electronic data storage device and the aforementioned computer.

TECHNICAL BACKGROUND

In e.g. deep brain stimulation (DBS), a new generation of electrodes can be implanted which are not rotationally symmetrical but have various orientational properties. Automatic detection of the orientation of such an electrode on postoperative images is aided by a favorable angle of the electrode axis relative to the imaging plane. However, in the case of more than one implanted electrode, the calculation of such an optimal imaging plane is counter-intuitive.

An algorithm within the planning application can calculate a so-called consensus plane or alert the user to the fact that for the given one or more planned trajectories no optimal scanning plane will be possible later, either due to the implantation angle of the electrodes or conflicts with certain scanning rules (e.g. radiation exposure to the eyes).

So far, use of either CT or rotational fluoroscopy for the purpose of orientation detection has been known. In both cases it has become apparent that the results depend strongly on the angle of the electrode relative to the imaging plane: in the case of CT the results become erratic for a large acute angle between the electrode axis and the imaging plane normal vector (e.g. above 40°, e.g. above 50°, or e.g. above 60°), whereas in rotational fluoroscopy they become less robust when the acute angle between the electrode axis and the imaging plane normal vector is less than for example 40° or for example 30°. Therefore, having scanning recommendations for intra- or postoperative scanning already at the planning stage is desirable.

Previous solutions focussed on orientation detection after completing the operation and the post-operative scans (resulting in radiation to the patient) had been taken. No optimization of the scanning parameters on the basis of electrode angles has so far been available.

The present invention has the object of providing for improved planning of a medical imaging procedure for rendering an improved image of a medical device such as an electrode.

The present invention can be used for planning imaging procedures e.g. in connection with a medical imaging device such as AIROR, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses determining a consensus plane for imaging an elongate medical device such as an electrode or a catheter. The consensus plane is an imaging plane having an optimal orientation relative to a characteristic geometric quantity of the elongate medical device such as the orientation of its longitudinal axis. When positioning an analytical device such as a medical imaging device (e.g. a tomographic scanner or a C-arm x-ray machine) such that its imaging plane is parallel to or coincides with the consensus plane, an optimal image of the elongate medical device can be generated. The consensus plane is determined by analysing patient image data used for planning an imaging procedure, planned trajectory data defining a planned position of the elongate medical device relative to the position of an anatomical body part, imaging device constraint data describing machine constraints governing operation of the medical imaging device, avoidance region position data defining the position of anatomical regions of the patient's body which comprise for example an organ-at-risk or an imaging artefact-generating structure such as an implant and shall not be influenced by the imaging radiation and for example not be intersected by the consensus plane in the case of a tomographic scan, and orientation condition data defining a boundary condition for an angle between the orientation of the consensus plane and the orientation of the characteristic geometric quantity (e.g. the longitudinal axis) of the elongate medical device.

A CT scanner can be used to perform imaging in a so-called "scout scan" mode, which is a radiographic imaging mode to acquire an image similar to an image acquired using a standard X-ray, e.g. a single image from a C-arm or a fluoroscopic device. Even though it is acquired using a CT scanner or other tomographic device, this is a projection image and not a tomographic image. In this case, the image and the respective imaging plane should be considered analogous to a radiographic image (projection) and not a tomographic reconstruction.

A standard X-ray in the context as used herein is a non-tomographic X-ray image being a projection.

GENERAL DESCRIPTION OF THE INVENTION

In this section, a description of the general features of the present invention is given for example by referring to possible embodiments of the invention.

In general, the invention reaches the afore-mentioned object by providing, in a first aspect, a computer-implemented medical method of determining a consensus plane usable for imaging an anatomical body part (and for example an elongate medical device, for example simultaneously together with the anatomical body part) with a medical imaging device. The method comprises executing, on at least one processor of at least one computer, the following exemplary steps which are constituted to be executed, for example are executed, by the at least one processor.

In a (for example first) exemplary step, patient image data is acquired which describes an anatomical body part of a patient's body. The patient image data describes for example a planning image of the anatomical body part. The planning image has for example been generated by applying a medical imaging modality such as magnetic resonance imaging or computed x-ray tomography, ultrasound tomography, or (for example two-dimensional) radiography or fluoroscopy (e.g. rotational fluoroscopy) to the anatomical body part. The anatomical body part can be any part of the patient's body and can comprise at least one of soft or bony tissue (the term of bony tissues encompassing cartilage). In examples, the anatomical body part is at least part of the brain, the head, the thorax or an internal organ such as the heart or lung or an intestinal organ such as the stomach or the colon. Generation of the patient image data may be part of the method according to the first aspect or may be executed before the method according to the first aspect is executed (i.e. the patient image data may serve as a mere input to the method according to the first aspect).

In a (for example second) exemplary step, planned trajectory data is acquired which describes an orientation of a longitudinal axis of an elongate medical device and a position of the medical device relative to the anatomical body part. For example, both the orientation and the position of the elongate medical device are defined relative to the anatomical body part, e.g. the position of the anatomical body part. The position and orientation of the elongate medical device define at least part of a planned trajectory for inserting the elongate medical device (which in one example is an electrode for deep brain stimulation, for example a directional or non-directional deep brain stimulation) into the anatomical body part. Generation of the planned trajectory data may be part of the method according to the first aspect or may be executed before the method according to the first aspect is executed (i.e. the planned trajectory data may serve as a mere input to the method according to the first aspect). The elongate medical device is for example an electrode, for example for at least one of electric stimulation or electric sensing in the anatomical body part, or for example a catheter, for example for drug delivery in the anatomical body part, or a combination of such an electrode and such a catheter.

In a (for example third) exemplary step, initial imaging plane data of a medical imaging device is determined based on the planned trajectory data. The initial imaging plane data describes a relative orientation between the orientation of the longitudinal axis of the elongate medical device and an imaging plane (also called initial imaging plane) of the medical imaging device which is for example useable for simultaneously imaging the medical device and the anatomical body part. The orientation of the imaging plane is defined by the normal vector on the imaging plane.

For a tomographic scan, the imaging plane is the plane that contains a cross-section of the imaged anatomical body part.

For non-tomographic radiography (e.g. from rotational fluoroscopy, C-arm, or rotational angiography) the imaging plane is a plane which has a normal parallel to the main axis of the radiation source and e.g. when a projection onto the imaging plane is performed it contains an image of the anatomical body part.

In the case of a computed x-ray tomograph as the imaging device, the imaging plane of the medical imaging device is a plane in which additionally at least some, in one example at least substantially all, of the beams of imaging radiation (e.g. ionising imaging radiation such as x-rays or non-ionising imaging radiation such as radio waves for conducting magnetic resonance tomography) to be emitted by the medical imaging device lie when the anatomical body part and/or the elongate medical device is imaged using the imaging radiation, i.e. the orientation of the imaging plane lies in at least one coordinate axis orthogonally to the plane in which the beams of imaging radiation lie (orthogonally to the beam directions). In the case of a C-arm as the imaging device, the orientation of the imaging plane additionally lies parallel (instead of orthogonally as for the CT case) to the beam direction, i.e. the beams intersect the imaging plane at a right angle. The medical imaging device may be a tomographic imaging device such as a magnetic resonance scanner or computed x-ray tomography scanner (for example, a computed x-ray tomography scanner configured to generate a multi-slice scan or a computed x-ray tomography scanner configured to generate a cone-beam scan) or may be a medical imaging device for conducting two-dimensional imaging such as C-arm for radiography.

In a (for example fourth) exemplary step, imaging device constraint data is acquired which describes a plurality of possible relative orientations between the imaging plane of the medical imaging device and an orientation of the longitudinal axis of the elongate medical device or the anatomical body part. For example, the imaging device constraint data describes machine constraints such as gantry tilt (e.g. a maximum gantry tilt) or couch tilt (e.g. a maximum couch tilt) or patient tilt (e.g. a maximum patient tilt) or position of the patient or the anatomical body part relative to the imaging device. In one example, the imaging device constraint data describes at least one degree of freedom or a plurality of degrees of freedom of the medical imaging device (for example, relative to the patient's body), for example at least one degree of freedom or a plurality of degrees of freedom acquired from constructional data of the medical imaging device. In one example, the imaging device constraint data describes a range of motion of at least one degree of freedom or of a plurality of degrees of freedom of the medical imaging device (for example, relative to the patient's body), for example of a degree of freedom or of a plurality of degrees of freedom acquired from constructional data of the medical imaging device.

In a (for example fifth) exemplary step, orientation condition data is acquired which describes a predetermined condition to be met by the relative orientation between the orientation of the longitudinal axis of the elongate medical device and the imaging plane of the medical imaging device. This relative orientation is defined for example by an angle between the axis of the elongate medical device and the imaging device constraint data, for example the imaging plane constraints or machine constraints. In one example, the predetermined condition comprises a boundary condition for the angle between the normal vector of the imaging plane of the medical imaging device and the orientation of the longitudinal axis of the medical device such as a value of the angle of (for example at least substantially, for example about or exactly, 40° or at least substantially, for example about or exactly, 50°, or at least substantially, for example about or exactly, 60°, for example about or exactly, 30°). The aforementioned angles depend for example on the geometry of the elongate medical device and depend for example on the imaging parameters.

In a (for example sixth) exemplary step, consensus plane data is determined based on the avoidance region position data and the imaging device constraint data and the initial imaging plane data and the orientation condition data. The consensus plane data describes a relative orientation between the imaging plane of the medical imaging device and the orientation of the longitudinal axis of the medical device, which orientation is to be applied for imaging the anatomical body part and the medical device (simultaneously, for example because the medical imaging device will have been inserted, for example implanted, into the anatomical body part) with the medical imaging device. Determining the consensus plane data encompasses for example determination of an optimal imaging position of the medical imaging device relative to the elongate medical device (for example, relative to the position of the elongate medical device) and an angle within the machine constraints of the medical imaging device and other (e.g. anatomical) constraints, such as the position of an avoidance region. The consensus plane is for example a plane to which the imaging plane is parallel or to which the imaging plane is identical when the imaging plane is oriented within the angular boundaries defined by the orientation condition data relative to a characteristic geometric quantity (for example, the orientation of the longitudinal axis of the elongate medical device) describing the geometry of an object to be imaged (for example, the elongate medical device). If the object is imaged in the consensus plane, an optimal image of the object is obtained—for example angular influences on the image appearance of the object can then be minimized. In an optimal case, the angle is 0°, i.e. the normal vector of the consensus plane is parallel to the longitudinal axis (specifically, the orientation of the longitudinal axis) of the elongate medical device. If the imaging device is a CT scanner. If the imaging device is a C-arm, the optimal case will be present if the normal vector of the consensus plane is orthogonal to the longitudinal axis (specifically, the orientation of the longitudinal axis) of the elongate medical device, in a specific example for all rotational positions of the C-arm for example relative to the elongate medical device.

For determining the consensus plane data, the orientation condition data provides information defining an angular boundary condition for the orientation of the consensus plane relative to the characteristic geometric quantity (such as the orientation of the longitudinal axis) of the elongate medical device. The boundary condition then is applied to the orientation of the initial imaging plane relative to the characteristic geometric quantity of each of the elongate medical devices simultaneously, i.e. a calculated imaging plane (such as an initial imaging plane) needs to fulfil the boundary condition(s) described by the orientation condition data with regard to the elongate medical device in order to be determined as (i.e. to be) a consensus plane.

The consensus plane data may in accordance with the method according to the first aspect also be determined for a plurality (e.g. two, for example exactly two) elongate medical devices simultaneously which are located at different positions relative to the position of the anatomical body part. In that case, the orientation condition data provides information for each of the elongate medical devices concerning an angular boundary condition for the orientation of the consensus plane relative to the characteristic geometric quantity (such as the orientation of the longitudinal axis) of each elongate medical device. The boundary condition then is applied to the orientation of the consensus plane relative to the characteristic geometric quantity of each of the elongate medical devices simultaneously, i.e. a calculated imaging plane (such as an initial imaging plane) needs to fulfil the boundary condition(s) described by the orientation condition data simultaneously with regard to each of the plurality of elongate medical devices in order to be determined as (i.e. to be) a consensus plane.

For example, avoidance region position data is acquired which describes the position of an avoidance region being an anatomical region. For example, the avoidance region lies within or outside of the anatomical body part. For example, the avoidance region comprises at least one of a position of an implant or an artefact-prone region (e.g. due to the presence of a metal implant in the avoidance region), a position of a risk organ (an organ-at-risk, abbreviated as OAR) such as an eye or a certain functional area of the brain). In one example, the avoidance region position data comprises implant position data that describes the relative position between a medical implant relative and the anatomical body part. The implant position data may be predetermined (for example, known) or automatically segmented e.g. by thresholding the planning image. For example, the avoidance region is an anatomical region in the anatomical body part which should (or is) at least substantially not be intersected by the imaging radiation. The avoidance region is an anatomical region which should be avoided by the imaging radiation, for example to avoid at least one of an imaging artefact or radiologic damage to the tissue lying in the avoidance region. Therefore, the avoidance region should not be intersected by the imaging radiation in the sense that the positions defining the avoidance region do at least substantially not overlap with the positions defining the imaging plane. For example, the set of positions (for example all positions) included in the imaging plane and the set of positions (for example all positions) defining the avoidance region shall not be subsets of one another.

For example, the avoidance region position data is determined based on at least one of the patient image data or atlas data. For example, the atlas data is acquired by the method according to the first aspect which describes a model (for example, a synthesized model such as an image-based model) of the patient' body, for example of at least the anatomical body part. The model may in examples be at least one of a standard patient model, generalized patient model, average patient model, or average human anatomy model. For example, the avoidance region position data may be determined by manually defining the avoidance region in the planning image (e.g. by user-interaction with the planning image) or by automatically determining the avoidance region in the planning image. The automatic determination of the avoidance region may be performed by at least one of segmenting the avoidance region in the planning image or by matching the atlas data with the patient image data, for by example by mapping an avoidance region known from the atlas data onto the patient image data (specifically, with the planning image). The mapping may be established to define a transformation between positional information of the atlas data and positional information of the patient image data so as to define a mapping of the position of the avoidance region in the atlas onto the position of the corresponding anatomical structure in the planning image. The mapping is for example accomplished by executing a fusion algorithm (for example, a rigid or elastic fusion algorithm) on the patient image data and the atlas data.

For example, the consensus plane data is determined by optimising the initial imaging plane data (for example the initial imaging plane) based on (for example in consideration of and/or by applying) the conditions defined by the avoidance region position data and the imaging device constraint data and the initial imaging plane data and the orientation condition data. Applicable optimization algorithms include constrained optimization algorithms such as convex relaxation methods, Newton's method, or the gradient descent method, which are solved by applying for example a deterministic approach, even though a probabilistic approach would in principle be possible.

In a further example, the method according to the first aspect comprises an exemplary step of outputting, for example displaying on a display device, information describing the content of the consensus plane data, for example by indicating, to a user, the relative orientation between the imaging plane of the medical imaging device and the orientation of the longitudinal axis of the medical device as at least one of a graphical (pictorial) rendering or as at least one human-readable numeric value or text value (string or character).

In a further example the method according to the first aspect comprises a step of determining, based on the consensus plane data, control data, wherein the control data comprises information for controlling the medical imaging device, wherein for example the medical imaging device is controlled based on the control data (i.e. by applying and/or executing the control data) such that its imaging plane (i.e. the imaging plane of the medical imaging device) attains the orientation relative to the orientation of the longitudinal axis of the medical device described by the consensus plane data.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention may alternatively or additionally relate to a (physical, for example electrical, for example technically generated) signal wave, for example a digital signal wave, carrying information which represents the program according to the second aspect and which for example comprises code means which are adapted to perform any or all of the steps of the method according to the first aspect.

In a fourth aspect, the invention is directed to a non-transitory computer-readable program storage medium on which the program according to the second aspect is stored.

In a fifth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the fourth aspect.

In a sixth aspect, the invention is directed to a medical system, comprising:
 a) the at least one computer according to the fourth aspect;
 b) at least one electronic data storage device storing at least the patient data and the imaging device constraint data; and
 c) the medical imaging device for imaging the anatomical body part and the elongate medical device,
  wherein the at least one computer is operably coupled to
   the at least one electronic data storage device for acquiring, from the at least one data storage device, at least the patient data and the imaging device constraint data, and
   the medical imaging device for issuing a control signal to the medical imaging device for controlling the operation of the medical imaging device on the basis of the consensus plane data.

In a seventh aspect, the present invention also relates to the use of the computer according to the fifth aspect or the system according to the sixth aspect or any embodiment thereof for determining a consensus plane for imaging an anatomical body part with a medical imaging device. The use comprises for example at least a step of executing at least one of the method according to the first aspect or the program according to the second aspect.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of inserting the elongate medical device or an implant into the patient's body. More particularly, the invention does not involve or in particular comprise or encompass any surgical or therapeutic activity. The invention is instead directed as applicable to planning a medical procedure, namely an imaging procedure for imaging the anatomical body part specifically by determining an applicable consensus plane for imaging the elongate medical device in the anatomical body part. Furthermore, the method according to the first aspect neither necessitates nor implies any imaging of the elongate medical device after inserting it into the anatomical body part. For this reason alone, no surgical or therapeutic activity and in particular no surgical or therapeutic step is necessitated or implied by carrying out the invention.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner.

The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination.

Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device).

Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy.

In order to distinguish the different data used by the present method, the data are denoted (i.e. referred to) as "XY data" and the like and are defined in terms of the information which they describe, which is then preferably referred to as "XY information" and the like.

The information on the imaging geometry preferably comprises information which allows the analysis image (x-ray image) to be calculated, given a known relative position between the imaging geometry analysis apparatus and the analysis object (anatomical body part) to be analysed by imaging radiation such as x-ray radiation or magnetic resonance radiation and/or radiowaves for generating nuclear magnetic resonance, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:
1. "An Efficient and Accurate Camera Calibration Technique for 3D Machine Vision", Roger Y. Tsai, Proceedings of the IEEE Conference on Computer Vision and Pattern Recognition. Miami Beach, Florida, 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. US 61/054,187

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

An analytical device such as a x-ray devices, a CT device or MRT device may be used to generate one or more analytical images (such as x-ray images or MRT images) of the body. For example, analytical devices are constituted to perform medical imaging methods. Analytical devices for example use medical imaging methods and are for example devices for analysing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray (also called radiography, cf. https://en.wikipedia.org/wiki/Radiography), medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
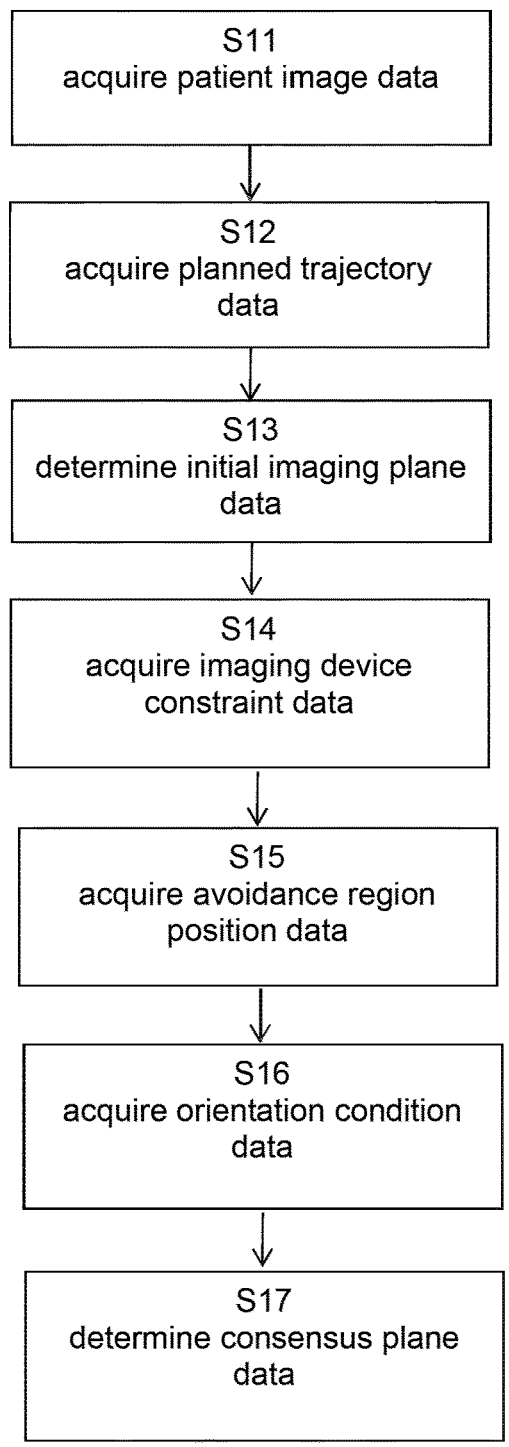
FIG. 1 illustrates a basic flow of the method according to the first aspect; is a flow diagram illustrating an embodiment of the method FIG. 2 according to the first aspect.

FIG. 1 illustrates the basic steps of the method according to the first aspect, in which step S11 encompasses acquisition of the patient image data, step S12 encompasses acquisition of the planned trajectory data, step S13 encompasses determination of the imaging plane data, subsequent step S14 encompasses acquisition of the imaging device constraint data, step S15 encompasses acquisition of the avoidance region position data, step S16 encompasses acquisition of the orientation condition data, and final step S17 encompasses determination of the consensus plane data.

Figure 2:
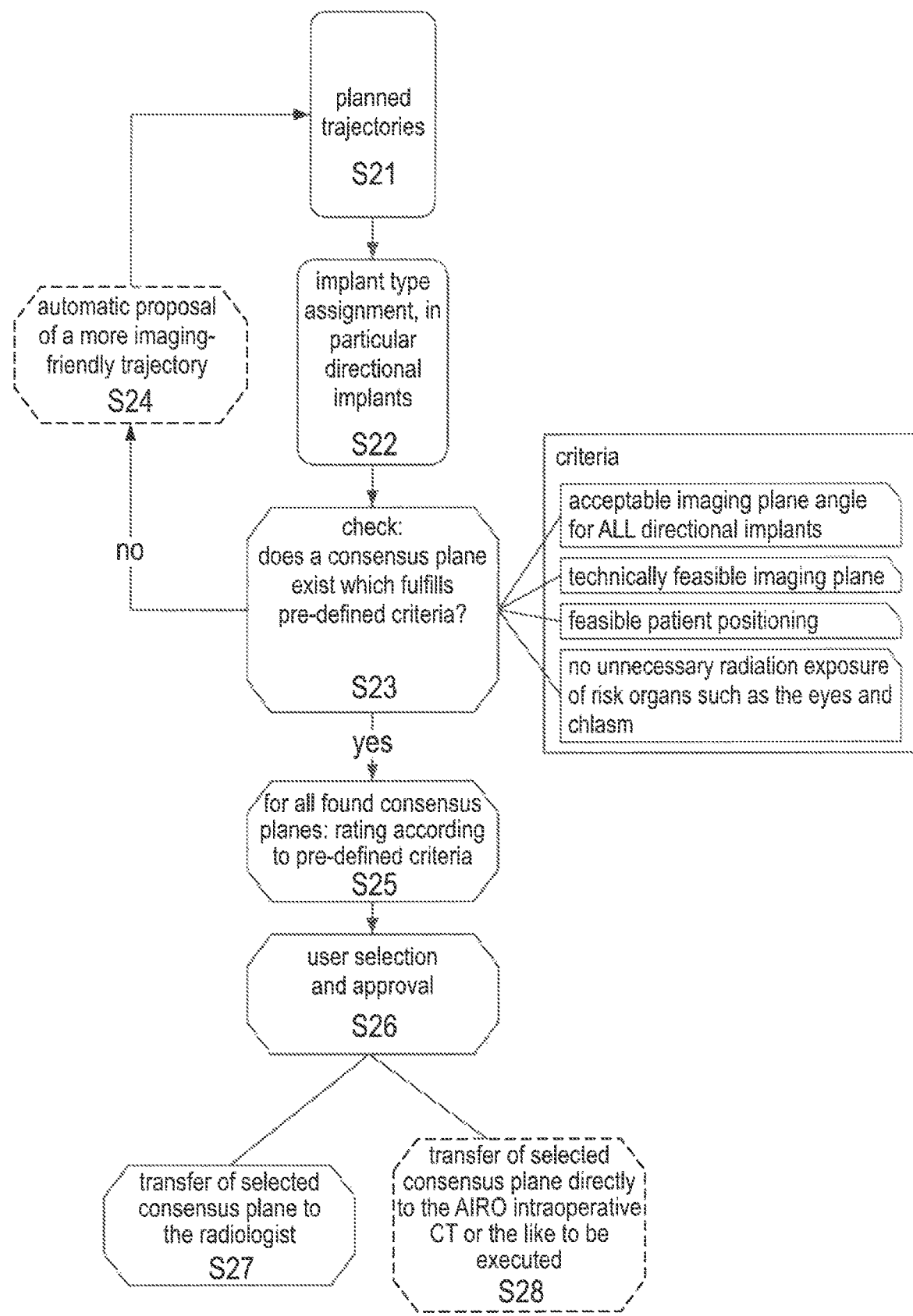

FIG. 2 describes an embodiment of the method according to the first aspect. In step S21, the implantation trajectories are pre-operatively planned and stored as the planned trajectory data. In step S22, the trajectories are selected which shall receive a directional implant. For those trajectories the system determines in step S23 whether a consensus plane exists which fulfils pre-defined criteria, e.g.:
- acceptable imaging plane angle for all directional implants
- the imaging plane is technically feasible
- the imaging plane does not require an uncomfortable or impossible patient positioning
- the imaging plane does not expose risk organs such as the eyes and chiasm to an unnecessary amount of radiation The result can be that there is more than one consensus plane. If the result of step S23 is that no consensus plane exists which fulfils the pre-defined criteria, the user is referred back to the planning stage of step S21 to choose a more imaging-friendly trajectory which is an automatically proposed in step S24. If the result of step S23 is that there is a consensus plane which fulfils the pre-defined criteria, each determined consensus plane is rated in step S25 according to pre-defined criteria and shown to the user for selection and approval in step S26. The selected consensus plane is then passed on to the radiologist in step S27 or sent directly as control data to the CT scanner to be executed in step S28.

This procedure removes uncertainty whether a given patient who shall later receive a directional implant can later can be supported in terms of programming through directionality visualization. Furthermore, this procedure holds the potential of minimizing unnecessary radiation exposure of the patient.

Figure 3:
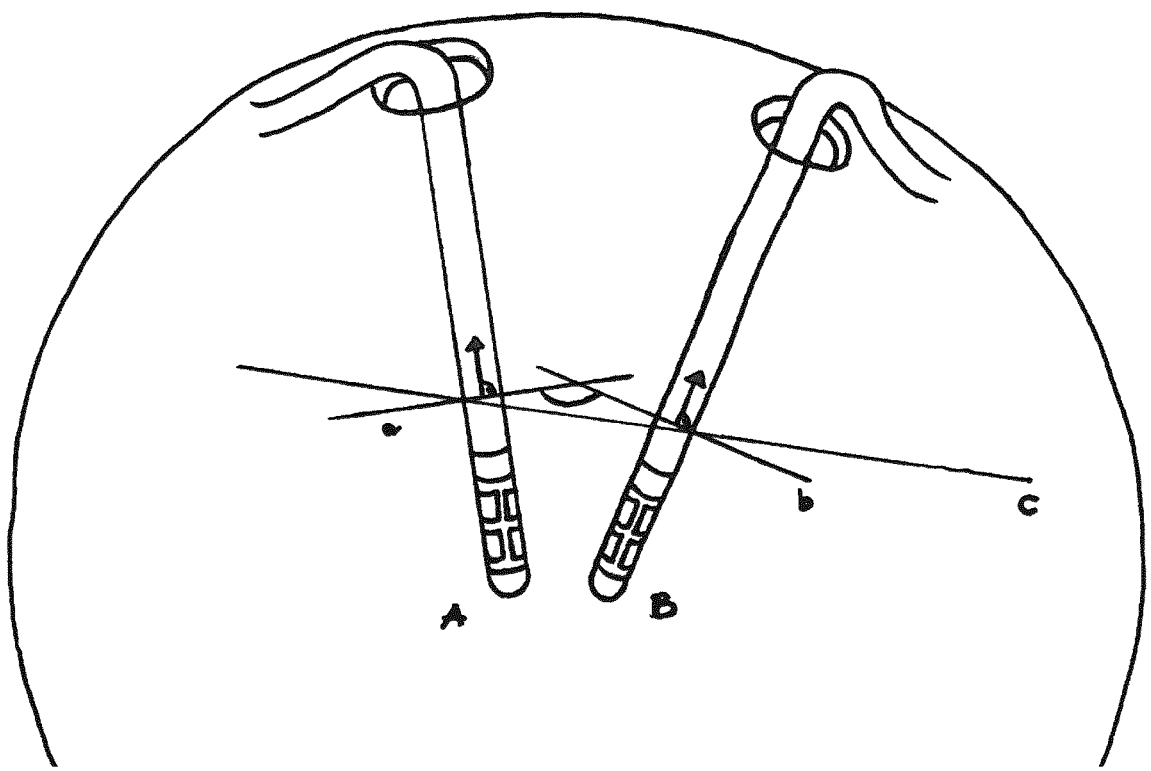
FIG. 3 is a schematic illustration of the geometric relations for determining a consensus plane simultaneously for two elongate medical devices.

FIG. 3 illustrates consensus planes a and b associated with each one two electrodes A and B, and common consensus plane c constituting a consensus plane applying simultaneously to both electrodes A and B. Consensus planes a and b lie in a plane perpendicular to the longitudinal axis of electrode A and B, respectively, while consensus plane c runs in an angle (or angles, respectively) relative to the longitudinal axes of electrodes A and B which is within the boundary or boundaries imposed by the orientation condition data.

Figure 4A:
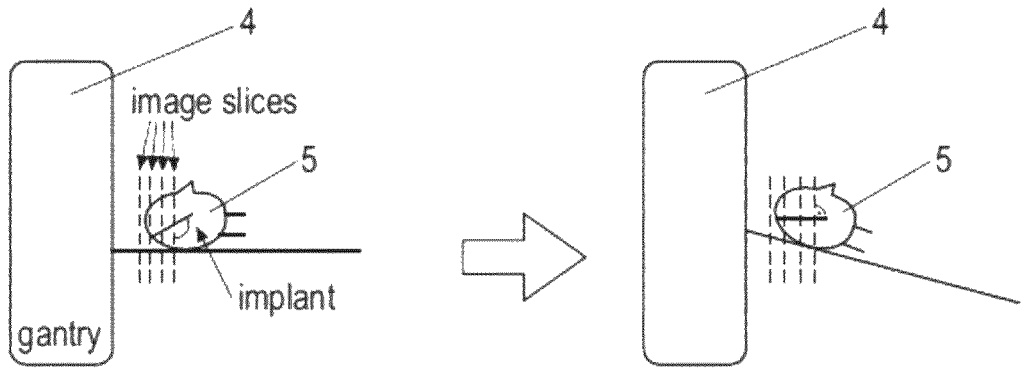
FIGS. 4a and 4b illustrate the location of the consensus plane for different types of medical imaging devices.

FIG. 4a shows re-positioning of the patient by moving the couch so that that image slices (shown in dashed lines) of a tomography generated with a medical imaging device embodied by a CT scanner 4 lies in a consensus plane relative to an elongate implant embodied by an electrode or a catheter in an anatomical body part embodied by the patient's head 5. The image slices lie in the consensus plane (i.e. coincide with or are parallel to the consensus plane) which runs in a direction perpendicular (orthogonal) to the longitudinal axis of the implant. From the left view to the right view, the patient couch is driven based on the above-described control data which has been determined on the basis of the consensus plane data so that the imaging plane of the CT scanner 4 lies in the consensus plane for imaging the implant.

Figure 4B:
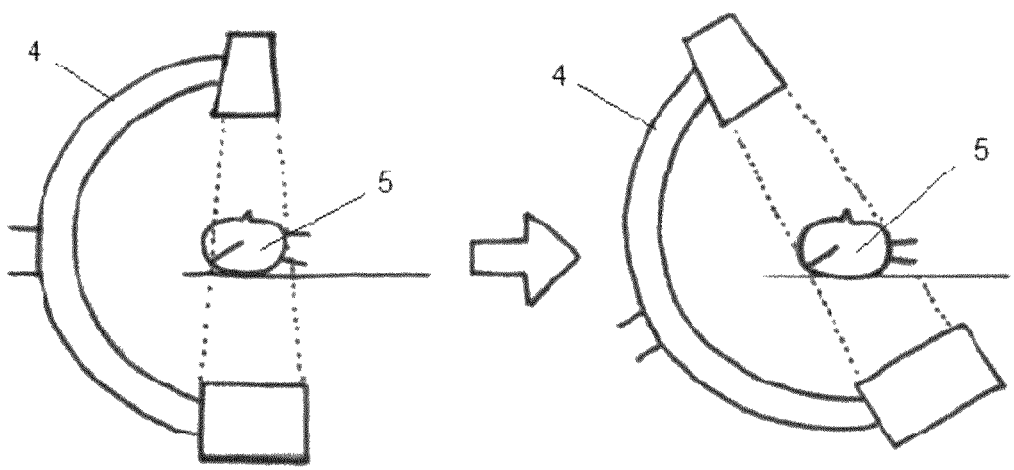

FIG. 4b shows re-positioning of the medical imaging device embodied by a C-arm x-ray machine 4 by moving the C-arm so that that the imaging plane of a radiography generated with the C-arm lies in a consensus plane relative to an elongate implant embodied by an electrode or a catheter in an anatomical body part embodied by the patient's head 5. The image thus generated lies in the consensus plane which runs in a direction parallel to the longitudinal axis of the implant (for example, the longitudinal axis of the implant lies in the consensus plane). From the left view to the right view, the C-arm is driven based on the above-described control data which has been determined on the basis of the consensus plane data so that the imaging plane of the C-arm 4 lies at least substantially in or at least substantially parallel to the consensus plane at least for one image in a rotational series of subsequently taken images.

Figure 5:
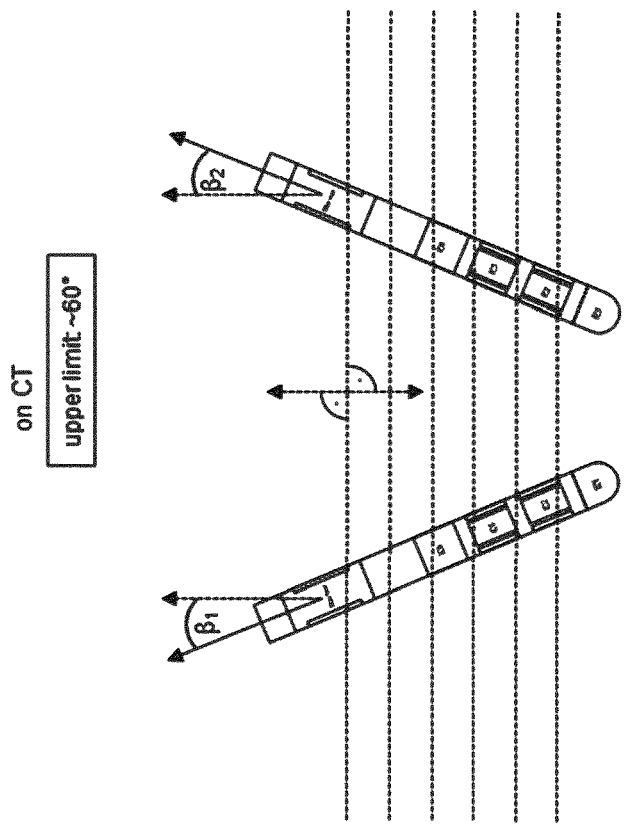
FIG. 5 illustrates limits of the relative orientation between the consensus plane and the longitudinal axis of two imaging devices.
Figure 5:
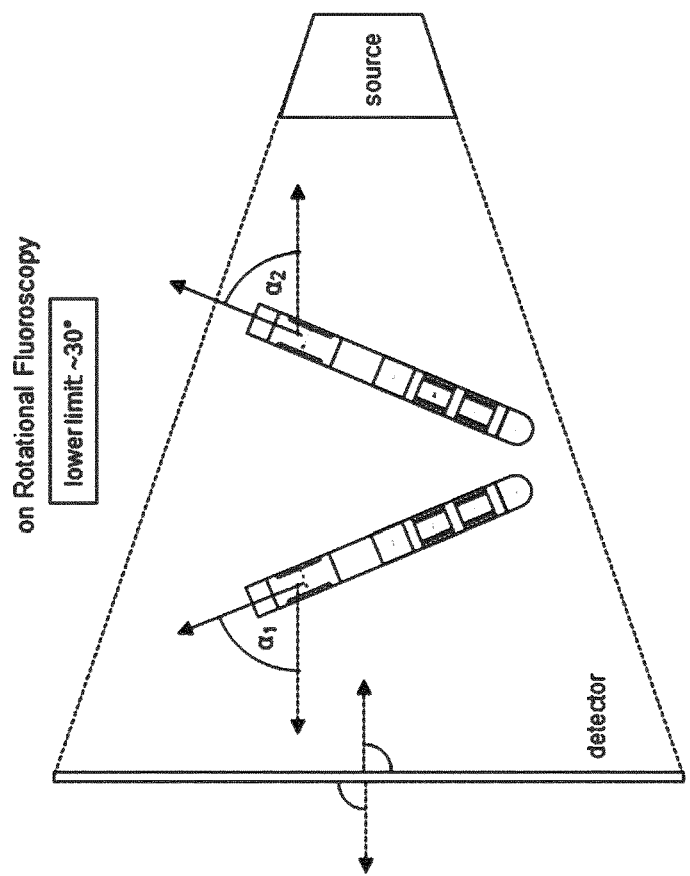
Figure 6:
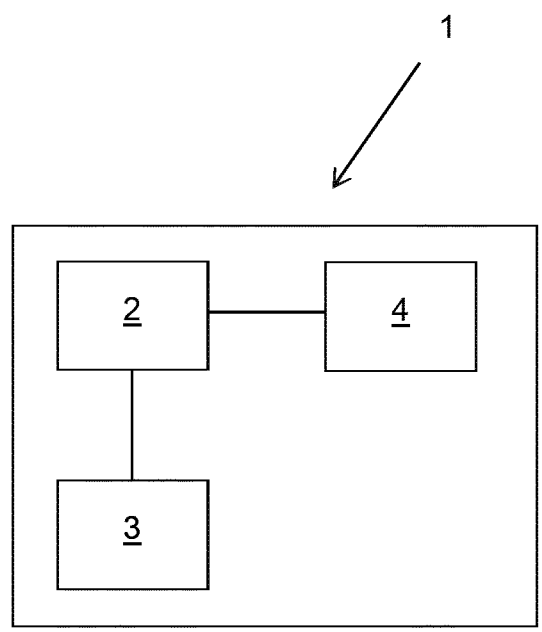
FIG. 6 is a schematic illustration of the system according to the sixth aspect.

FIG. 5 illustrates the limits for the angular boundary condition described by the orientation condition data. $\alpha_1$, $\alpha_2$, $\beta_1$, $\beta_2$ each depict an acute angle between the imaging plane normal and the axis of the elongate medical device. For a rotational fluoroscopy (generated for example by using a C-arm x-ray machine), a (minimum) acute angle $\alpha_1$, $\alpha_2$ between the orientation of the longitudinal axis of the elongate medical device and the normal of the imaging plane which is indicated by dashed arrows throughout FIG. 5 should be at least approximately 30° if that imaging plane is to be determined to be a consensus plane. For a computed x-ray tomography, this (maximum) acute angle $\beta_1$, $\beta_2$ should be equal to or smaller than approximately 60°. The aforementioned angles depend for example on the geometry of the elongate medical device and the imaging parameters FIG. 6 is a schematic illustration of the medical system 1 according to the sixth aspect. The system is in its entirety identified by reference sign 1 and comprises a computer 2, an electronic data storage device (such as a hard disc) 3 for storing at least the patient data and a medical imaging device 4 (such as). The components of the medical system 1 have the functionalities and properties explained above with regard to the sixth aspect of this disclosure.

The invention claimed is:

1. A computer-implemented method of determining a consensus plane usable for imaging an anatomical body part with a medical imaging device, the method comprising:
acquiring patient image data which describes an anatomical body part of a patient's body;
acquiring planned trajectory data which describes an orientation of a longitudinal axis of an elongate medical device and a position of the elongate medical device relative to the anatomical body part;
determining initial imaging plane data of the medical imaging device based on the planned trajectory data, wherein the initial imaging plane data describes a relative orientation between the orientation of the longitudinal axis of the elongate medical device and an imaging plane of the medical imaging device useable for simultaneously imaging the elongate medical device and the anatomical body part;
acquiring imaging device constraint data which describes a plurality of possible relative orientations between the imaging plane of the medical imaging device and an orientation of the longitudinal axis of the elongate medical device or the anatomical body part;
acquiring orientation condition data which describes a predetermined condition to be met by the relative orientation between the orientation of the longitudinal axis of the elongate medical device and the imaging plane of the medical imaging device;
determining consensus plane data based on the imaging device constraint data and the initial imaging plane data and the orientation condition data, wherein the consensus plane data describes a relative orientation between the imaging plane of the medical imaging device and the orientation of the longitudinal axis of the elongate medical device, which orientation is to be applied for imaging the anatomical body part and the elongate medical device with the medical imaging device; and acquiring avoidance region position data which describes a position of an avoidance region, wherein the avoidance region is a region in the anatomical body part, wherein the region shall at least substantially not be intersected by imaging radiation during the imaging, wherein the determining consensus plane data is further based on the avoidance region position data.

2. The method according to claim 1, wherein the acquiring avoidance region position data comprises determining avoidance region position data based on the patient image data.

3. The method according to claim 1, wherein the acquiring avoidance region position data comprises determining avoidance region position data based on atlas data.

4. The method according to claim 1, wherein the determining consensus plane data comprises determining consensus plane data by optimising the initial imaging plane data based on conditions defined by the avoidance region position data and the imaging device constraint data and the initial imaging plane data and the orientation condition data.

5. The method according to claim 1, wherein the predetermined condition comprises a boundary condition for an angle between the imaging plane of the medical imaging device and the orientation of the longitudinal axis of the elongate medical device.

6. The method according to claim 1, wherein the elongate medical device is an electrode, or a catheter, or a combination thereof.

7. The method according to claim 6, wherein the electrode is for at least one of electric stimulation or electric sensing in the anatomical body part, and wherein the catheter is for drug delivery in the anatomical body part.

8. The method according to claim 1, wherein the anatomical body part comprises at least part of a brain.

9. The method according to claim 1, wherein the acquiring avoidance region position data comprises acquiring avoidance region position data comprising implant position data describing a relative position between a medical implant and the anatomical body part.

10. The method according to claim 1, wherein the acquiring imaging device constraint data comprises acquiring imaging device constraint data that describes at least one degree of freedom of the medical imaging device.

11. The method according to claim 10, wherein the imaging device constraint data describes at least one degree of freedom acquired from constructional data of the medical imaging device.

12. The method according to claim 1, wherein the acquiring imaging device constraint data comprises acquiring imaging device constraint data that describes a range of motion of at least one degree of freedom of the medical imaging device.

13. The method according to claim 12, wherein the imaging device constraint data describes the range of motion of at least one degree of freedom acquired from constructional data of the medical imaging device.

14. The method according to claim 1, further comprising: determining control data based on the consensus plane data, wherein the control data comprises information for controlling the medical imaging device.

15. The method according to claim 14, further comprising:
generating a control signal for controlling, based on the control data, the medical imaging device such that the imaging plane attains the orientation relative to the orientation of the longitudinal axis of the elongate medical device described by the consensus plane data.

16. The method according to claim 1, further comprising:
outputting information describing content of the consensus plane data, wherein the outputting information comprises indicating the relative orientation between the imaging plane of the medical imaging device and the orientation of the longitudinal axis of the elongate medical device.

17. The method according to claim 16, wherein the outputting information comprises displaying, on a display device, the information describing content of the consensus plane data, the displaying the information comprises indicating the relative orientation between the imaging plane of the medical imaging device and the orientation of the longitudinal axis of the elongate medical device.

18. A non-transitory computer readable storage medium storing a program comprising program instructions, that when executed on at least one processor of a computer or loaded onto the at least one processor of the computer, causes the computer to perform a method of determining a consensus plane usable for imaging an anatomical body part with a medical imaging device by:

acquiring patient image data which describes an anatomical body part of a patient's body;

acquiring planned trajectory data which describes an orientation of a longitudinal axis of an elongate medical device and a position of the elongate medical device relative to the anatomical body part;

determining initial imaging plane data of the medical imaging device based on the planned trajectory data, wherein the initial imaging plane data describes a relative orientation between the orientation of the longitudinal axis of the elongate medical device and an imaging plane of the medical imaging device useable for simultaneously imaging the elongate medical device and the anatomical body part;

acquiring imaging device constraint data which describes a plurality of possible relative orientations between the imaging plane of the medical imaging device and an orientation of the longitudinal axis of the elongate medical device or the anatomical body part;

acquiring orientation condition data which describes a predetermined condition to be met by the relative orientation between the orientation of the longitudinal axis of the elongate medical device and the imaging plane of the medical imaging device;

determining consensus plane data based on the imaging device constraint data and the initial imaging plane data and the orientation condition data, wherein the consensus plane data describes a relative orientation between the imaging plane of the medical imaging device and the orientation of the longitudinal axis of the elongate medical device, which orientation is to be applied for imaging the anatomical body part and the elongate medical device with the medical imaging device; and acquiring avoidance region position data describing a position of an avoidance region, wherein the avoidance region is a region in the anatomical body part, wherein the region shall at least substantially not be intersected by imaging radiation during the imaging, wherein the determining consensus plane data is further based on the avoidance region position data.

19. A medical system, comprising:
at least one computer;
at least one electronic data storage device storing at least patient data and imaging device constraint data; and
a medical imaging device for imaging an anatomical body part and an elongate medical device,
wherein the at least one computer is operable to:
- acquire patient image data which describes an anatomical body part of a patient's body;
- acquire planned trajectory data which describes an orientation of a longitudinal axis of the elongate medical device and a position of the elongate medical device relative to the anatomical body part;
- determine initial imaging plane data of the medical imaging device based on the planned trajectory data, wherein the initial imaging plane data describes a relative orientation between the orientation of the longitudinal axis of the elongate medical device and an imaging plane of the medical imaging device useable for simultaneously imaging the elongate medical device and the anatomical body part;
- acquire, from the at least one electronic data storage device, imaging device constraint data which describes a plurality of possible relative orientations between the imaging plane of the medical imaging device and an orientation of the longitudinal axis of the elongate medical device or the anatomical body part;
- acquire orientation condition data which describes a predetermined condition to be met by the relative orientation between the orientation of the longitudinal axis of the elongate medical device and the imaging plane of the medical imaging device;
- determine consensus plane data based on the imaging device constraint data and the initial imaging plane data and the orientation condition data, wherein the consensus plane data describes a relative orientation between the imaging plane of the medical imaging device and the orientation of the longitudinal axis of the elongate medical device, which orientation is to be applied for imaging the anatomical body part and the elongate medical device with the medical imaging device; and
- acquire avoidance region position data describing the position of an avoidance region, wherein the avoidance region is a region in the anatomical body part, wherein the region shall at least substantially not be intersected by imaging radiation during the imaging,
- wherein the at least one computer is operable to determine the consensus plane data further based on the avoidance region position data,
- wherein the at least one computer is operable to issue a control signal to the medical imaging device for controlling operation of the medical imaging device based on the consensus plane data.

20. The medical system of claim 19, wherein the at least one computer is operable to determine consensus plane data by optimising the initial imaging plane data based on conditions defined by the avoidance region position data and the imaging device constraint data and the initial imaging plane data and the orientation condition data.

* * * * *